(12) United States Patent
Besnard

(10) Patent No.: US 12,029,906 B2
(45) Date of Patent: Jul. 9, 2024

(54) COCHLEAR IMPLANT HEARING AID SYSTEM

(71) Applicant: Cochlear Limited, Macquaire University (DK)

(72) Inventor: Martin Besnard, Vallauris (FR)

(73) Assignee: Cochlear Limited, Macquarie University (AU)

( * ) Notice: Subject to any disclaimer, the term of this patent is extended or adjusted under 35 U.S.C. 154(b) by 795 days.

(21) Appl. No.: 17/116,679

(22) Filed: Dec. 9, 2020

(65) Prior Publication Data
US 2021/0170173 A1    Jun. 10, 2021

(30) Foreign Application Priority Data

Dec. 10, 2019    (EP) .................................... 19214859

(51) Int. Cl.
*A61N 1/36*    (2006.01)
*H04R 25/00*   (2006.01)
*A61N 1/05*    (2006.01)

(52) U.S. Cl.
CPC ....... *A61N 1/36038* (2017.08); *H04R 25/505* (2013.01); *H04R 25/554* (2013.01); *A61N 1/0541* (2013.01); *H04R 2225/43* (2013.01); *H04R 2225/67* (2013.01)

(58) Field of Classification Search
CPC .............. A61N 1/36038; A61N 1/0541; H04R 25/505; H04R 25/554; H04R 2225/43; H04R 2225/67
See application file for complete search history.

(56) References Cited

U.S. PATENT DOCUMENTS

| | | | |
|---|---|---|---|
| 8,855,554 B2 | 10/2014 | Cook et al. | |
| 9,094,055 B2* | 7/2015 | Low | H02J 50/12 |
| 9,820,061 B2* | 11/2017 | Fort | H04R 25/43 |
| 2012/0267960 A1 | 10/2012 | Low et al. | |
| 2014/0035384 A1 | 2/2014 | Satyamoorthy et al. | |

(Continued)

*Primary Examiner* — Shirley X Jian
(74) *Attorney, Agent, or Firm* — Edell, Shapiro & Finnan, LLC

(57) ABSTRACT

A cochlear implant hearing aid system is disclosed. The system comprises an external unit configured to receive acoustic sound and process the acoustic sound into a coded audio signal, and an implantable unit configured to receive the coded audio signal. Further, the external unit comprises a power supply unit connected via a first path to a switching unit, wherein the switching unit is connected via a second path to ground and is connected at an output thereof to a first coil. Furthermore, the switching unit is configured to operate as a switching element configured to switch between switching states, wherein the switching states include a first state for applying and a second state for not applying a current to the first coil. The coded audio signal is supplied to the switching unit as a control signal, and the first coil is inductively linked to a second coil arranged in the implantable unit. The system further comprises a measuring unit connected to at least one of the first and second paths and configured to measure a dissipative current occurring in relation to the switching states of the switching unit. Based on the at least one measured dissipative current, a resonance frequency of the inductive link between the first and second coils is adapted.

12 Claims, 8 Drawing Sheets

(56) References Cited

U.S. PATENT DOCUMENTS

2014/0270296 A1    9/2014   Fort et al.
2015/0341087 A1   11/2015   Moore et al.
2020/0121920 A1*   4/2020   Riis ..................... A61N 1/3756

* cited by examiner

COCHLEAR IMPLANT HEARING AID SYSTEM

FIELD

The present disclosure relates to a cochlear implant hearing aid system. More particularly, to such a system equipped with a dissipative current measuring unit, and to a method for a cochlear implant hearing aid system with a dissipative current measuring unit.

BACKGROUND

Cochlear implants (CIs) are devices containing electrodes inserted in the inner ear (the cochlea) to recover the sensation of audition to people suffering from severe to profound hearing loss. CIs are bypassing most of the functional hearing chain, and generate a series of electrical pulse train inside the cochlea to initiate action potentials from the hair cells. Those devices are thus mostly considered as biocompatible electronic machines. Depending on their implementation, they can either be totally implanted, or composed of two main parts. A first part is the sound processor, often placed near the ear. It contains microphones that capture the environmental sound, which is processed in real time into a series of codes usable by the second part, implanted into the patient. The implant receives both power and sound information though radiofrequency from the sound processor, and generates electrical pulses sent into the cochlea via electrodes inside the cochlea.

Reducing power losses occurring in the sound processor defines a topic of high interest, but is as such often quite difficult to achieve. However, prior to reducing such power losses, identification thereof is often an even bigger challenge.

Therefore, there is a need to provide a solution that addresses at least some of the above-mentioned problems.

SUMMARY

According to an aspect, a cochlear implant hearing aid system is disclosed. The system comprises an external unit configured to receive acoustic sound and process the acoustic sound into a coded audio signal, and an implantable unit configured to receive the coded audio signal. Further, the external unit comprises a power supply unit connected via a first path to a switching unit, wherein the switching unit is connected via a second path to ground and is connected at an output thereof to a first coil. Furthermore, the switching unit is configured to operate as a switching element configured to switch between switching states, wherein the switching states include a first state for applying and a second state for not applying a current to the first coil. The coded audio signal is supplied to the switching unit as a control signal, and the first coil is inductively linked to a second coil arranged in the implantable unit. The system further comprises a measuring unit connected to at least one of the first and second paths and configured to measure a dissipative current occurring in relation to the switching states of the switching unit. Based on the at least one measured dissipative current, a resonance frequency of the inductive link between the first and second coils is adapted.

This allows for adapting the resonance frequency (herein below also referred to as tuning of the switching unit) based on measured dissipative currents.

Particularly, such cochlear implant hearing aid system further allows for measuring a tuning/mistuning (no occurrence/occurrence of dissipative current) of the switching unit. As a result thereof, by usage of one measurement, it is directly derivable which type of first and second coils (antennas) to use for establishing the inductive link between the external unit and the implantable unit, thereby for example addressing patients with different skin thicknesses by distinguishing e.g. between skin thickness ranges of 1 mm to 6 mm and 4 mm to 11 mm.

Specifically, the cochlear implant hearing aid system further allows for monitoring an adaptation of the resonance frequency, and even further allows for continuously monitoring the adaptation during use of the cochlear implant hearing aid system, which is unique for a cochlear implant hearing aid system. This leads to even further improve power efficiency of the system, since the inductive link becomes more efficient due to the ability of continuously adapting the resonance frequency (keeping the resonance frequency of the first coil aligned or almost aligned to a target resonance frequency). In particular, the resonance frequency of the first coil is adapted in order to minimize the at least one measured dissipative current.

As result of continuously monitoring a resonance frequency adaptation, adaptation of the resonance frequency (tuning of the switching unit) may be performed in real time, allowing for reducing power losses even further.

Furthermore, the first path may further comprise a shunt resistor, and the measuring unit may further be configured to measure the dissipative current across the shunt resistor. Moreover, the measuring unit may further comprise an amplification element configured to amplify a current to be measured by the measuring unit.

Optionally, the second path may further comprise a third coil inductively coupled to a fourth coil, and the measuring unit comprises the fourth coil and may further be configured to measure a current induced in the fourth coil and to derive the dissipative current therefrom. Optionally, the measuring unit is further configured to comprise an amplification element configured to amplify the current induced in the fourth coil. Furthermore, the measuring unit may further be configured to comprise a resistor connected to an output of the amplification element and a capacitor connected at one out of its terminals to the connection between the output of the amplification element and the resistor and at the other one of its terminals to ground.

Such measuring unit configurations as outlined above each allow for simplicity of a design of the measuring unit, by exploiting existing components of the switching unit and/or the cochlear implant hearing aid system. Particularly, by using the existing components, application of new components to the switching unit/cochlear implant hearing aid system is therefore avoidable, which leads to a more complex design of the measuring unit.

In addition, this further allows for avoiding that the measuring unit has an impact on the switching unit adapting the resonance frequency, as well as for avoiding that the measuring unit creates a parasitic resistance to the circuitry constituting the switching unit/cochlear implant hearing aid system.

Moreover, the switching unit may for example be an E-Class amplifier.

This allows for theoretically 100% efficiency of the switching unit, which means no power losses and, therefore, no dissipative current in the transistor constituting the E-Class amplifier.

According to at least an implementation, the resonance frequency of the inductive link may be adapted based on the at least one measured dissipative current by selectively connecting at least one further switched capacitor to a circuitry constituting the switching unit.

Optionally, according to a further implementation, the switching unit may further comprise at least one of a first switched capacitor and a second switched capacitor, wherein the first switched capacitor is connected in parallel to a first circuitry element, and the second switched capacitor is connected in serial to a second circuitry element. Further, the resonance frequency is adapted based on the at least one measured dissipative current by selectively connecting at least one of the first and second switched capacitors to the circuitry constituting the switching unit.

Furthermore, the switching unit may further comprise a transistor element, wherein the transistor element is connected at an output thereof via the first circuitry element to ground, and via the second circuitry element to the first coil. Further, the first circuitry element may be a third capacitor, and the second circuitry element may be a fourth capacitor.

Applying a switched capacitor for adapting the resonance frequency during the above mentioned monitoring process allows for adjusting a tuning of the switching unit in real time.

According to another aspect, a method for a cochlear implant hearing aid system comprising an external unit receiving acoustic sound and processing the acoustic sound into a coded audio signal and an implantable unit receiving the coded audio signal is disclosed. The method comprises the steps of supplying in the external unit power from a power supply unit via a first path to a switching unit, wherein the switching unit is connected via a second path to ground and is connected at an output thereof to a first coil. Further, the switching unit operates as a switching element to switch between switching states, wherein the switching states include a first state for applying and a second state for not applying a current to the first coil. The coded audio signal is supplied to the switching unit as a control signal, and the first coil is inductively linked to a second coil arranged in the implantable unit. The method further comprises the steps of measuring across at least one of the first and second paths a dissipative current occurring in relation to the switching states of the switching unit. The method further comprises adapting a resonance frequency of the inductive link between the first and second coils based on the at least one measured dissipative current.

This allows for a method for adapting the resonance frequency based on measuring at least one dissipative current.

Particularly, as derivable from above, such method for a cochlear implant hearing aid system further allows for measuring a tuning/mistuning of the switching unit and further allows for monitoring a resonance frequency adaptation, especially during use of the cochlear implant hearing aid system, which is unique for a cochlear implant hearing aid system. Such method therefore leads to even further improving power efficiency of the system, since the inductive link becomes more efficient due to continuously adapting the resonance frequency, which allows for real time resonance frequency adaptation, allowing for reducing power losses even further.

In addition, the method may further comprise the steps of measuring a first dissipative current across a shunt resistor contained in the first path, and/or measuring a second dissipative current based on a current induced in a fourth coil inductively coupled to a third coil, wherein the third coil is comprised in the second path.

This allows for a method for measuring a dissipative current, by exploiting existing components of the switching unit and/or the cochlear implant hearing aid system. Particularly, by applying the method on the existing components, application of new components to the switching unit/cochlear implant hearing aid system is therefore avoidable, which leads to a more simplified measurement.

This further allows for a method for avoiding the measurement having an impact on a tuning of the switching unit, as well as for avoiding the measurement creating a parasitic resistance to the circuitry constituting the switching unit/cochlear implant hearing aid system.

Furthermore, the method may further comprise the steps of deriving a weighted dissipative current from the measured first and second dissipative currents based on applying a predetermined weighting algorithm. Further, the method comprises adapting the resonance frequency of the inductive link based on the derived weighted dissipative current.

This allows for increasing accuracy in resonance frequency adaptation (in tuning of the switching unit).

Moreover, the method may further comprise the steps of adapting the resonance frequency of the inductive link based on the at least one measured dissipative current by selectively connecting at least one further switched capacitor to a circuitry constituting the switching unit.

Optionally, the switching unit further comprises at least one of a first switched capacitor and a second switched capacitor, wherein the first switched capacitor is connected in parallel to a first circuitry element, and the second switched capacitor is connected in serial to a second circuitry element. The method may further comprises the steps of adapting the resonance frequency of the inductive link based on the at least one measured dissipative current by selectively connecting at least one of the first and second switched capacitors to the circuitry constituting the switching unit. The switching unit may be an E-Class amplifier and further comprises a transistor element, wherein the transistor element is connected at an output thereof via the first circuitry element to ground, and at an output thereof via the second circuitry element to the first coil. Further first circuitry element may be a third capacitor and the second circuitry element may be a fourth capacitor.

Applying a switched capacitor for adapting the resonance frequency during the above mentioned monitoring process allows for a method for adjusting a tuning of the switching unit in real time.

BRIEF DESCRIPTION OF DRAWINGS

The aspects of the disclosure may be best understood from the following detailed description taken in conjunction with the accompanying figures. The figures are schematic and simplified for clarity, and they just show details to improve the understanding of the claims, while other details are left out. Throughout, the same reference numerals are used for identical or corresponding parts. The individual features of each aspect may each be combined with any or all features of the other aspects. These and other aspects, features and/or technical effect will be apparent from and elucidated with reference to the illustrations described hereinafter in which:

DETAILED DESCRIPTION

Figure 1:
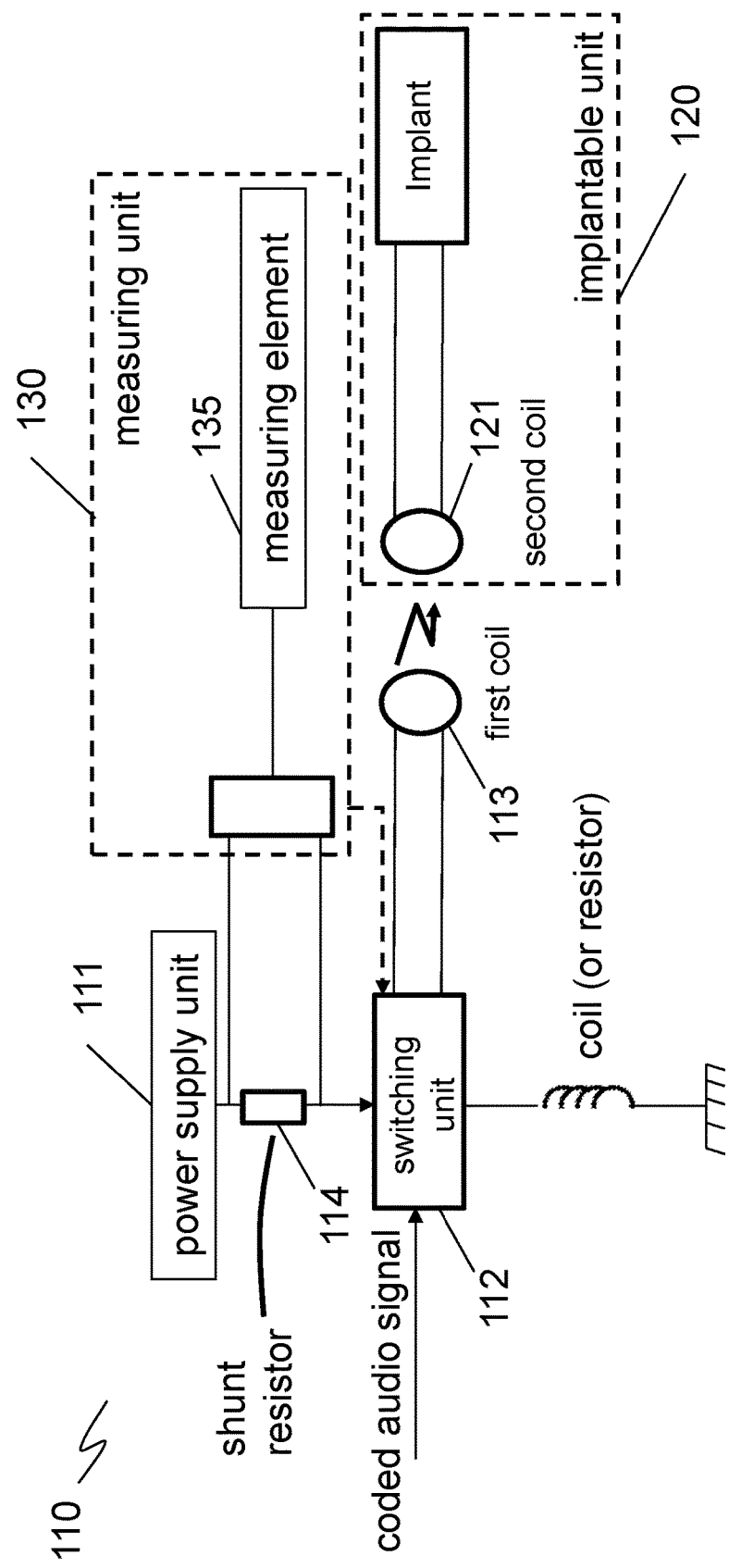
FIG. 1 illustrates a schematic diagram of a cochlear implant hearing aid system according to a first embodiment of the disclosure.

The detailed description set forth below in connection with the appended drawings is intended as a description of various configurations. The detailed description includes specific details for the purpose of providing a thorough understanding of various concepts. However, it will be apparent to those skilled in the art that these concepts may be practised without these specific details. Several aspects of the apparatus and methods are described by various blocks, functional units, modules, components, circuits, steps, processes, algorithms, etc. (collectively referred to as "elements"). Depending upon particular application, design constraints or other reasons, these elements may be implemented using electronic hardware, computer program, or any combination thereof.

The electronic hardware may include microprocessors, microcontrollers, digital signal processors (DSPs), field programmable gate arrays (FPGAs), programmable logic devices (PLDs), gated logic, discrete hardware circuits, and other suitable hardware configured to perform the various functionality described throughout this disclosure. Computer program shall be construed broadly to mean instructions, instruction sets, code, code segments, program code, programs, subprograms, software modules, applications, software applications, software packages, routines, subroutines, objects, executables, threads of execution, procedures, functions, etc., whether referred to as software, firmware, middleware, microcode, hardware description language, or otherwise.

A hearing device may include a hearing aid that is adapted to improve or augment the hearing capability of a user by receiving an acoustic signal from a user's surroundings, generating a corresponding audio signal, possibly modifying the audio signal and providing the possibly modified audio signal as an audible signal to at least one of the user's ears. The "hearing device" may further refer to a device such as an earphone or a headset adapted to receive an audio signal electronically, possibly modifying the audio signal and providing the possibly modified audio signals as an audible signal to at least one of the user's ears. Such audible signals may be provided in the form of an acoustic signal radiated into the user's outer ear, or an acoustic signal transferred as mechanical vibrations to the user's inner ears through bone structure of the user's head and/or through parts of middle ear of the user or electric signals transferred directly or indirectly to cochlear nerve and/or to auditory cortex of the user.

The hearing device is adapted to be worn in any known way. This may include i) arranging a unit of the hearing device behind the ear with a tube leading air-borne acoustic signals into the ear canal or with a receiver/loudspeaker arranged close to or in the ear canal such as in a Behind-the-Ear type hearing aid, and/or ii) arranging the hearing device entirely or partly in the pinna and/or in the ear canal of the user such as in a In-the-Ear type hearing aid or In-the-Canal/Completely-in-Canal type hearing aid, or iii) arranging a unit of the hearing device attached to a fixture implanted into the skull bone such as in Bone Anchored Hearing Aid or Cochlear Implant, or iv) arranging a unit of the hearing device as an entirely or partly implanted unit such as in Bone Anchored Hearing Aid or Cochlear Implant.

A "hearing system" refers to a system comprising one or two hearing devices, and a "binaural hearing system" refers to a system comprising two hearing devices where the devices are adapted to cooperatively provide audible signals to both of the user's ears. The hearing system or binaural hearing system may further include auxiliary device(s) that communicates with at least one hearing device, the auxiliary device affecting the operation of the hearing devices and/or benefitting from the functioning of the hearing devices. A wired or wireless communication link between the at least one hearing device and the auxiliary device is established that allows for exchanging information (e.g. control and status signals, possibly audio signals) between the at least one hearing device and the auxiliary device. Such auxiliary devices may include at least one of remote controls, remote microphones, audio gateway devices, mobile phones, public-address systems, car audio systems or music players or a combination thereof. The audio gateway is adapted to receive a multitude of audio signals such as from an entertainment device like a TV or a music player, a telephone apparatus like a mobile telephone or a computer, a PC. The audio gateway is further adapted to select and/or combine an appropriate one of the received audio signals (or combination of signals) for transmission to the at least one hearing device. The remote control is adapted to control functionality and operation of the at least one hearing devices. The function of the remote control may be implemented in a SmartPhone or other electronic device, the SmartPhone/electronic device possibly running an application that controls functionality of the at least one hearing device.

In general, a hearing device includes i) an input unit such as a microphone for receiving an acoustic signal from a user's surroundings and providing a corresponding input audio signal, and/or ii) a receiving unit for electronically receiving an input audio signal. The hearing device further includes a signal processing unit for processing the input audio signal and an output unit for providing an audible signal to the user in dependence on the processed audio signal.

The input unit may include multiple input microphones, e.g. for providing direction-dependent audio signal processing. Such directional microphone system is adapted to enhance a target acoustic source among a multitude of acoustic sources in the user's environment. In one aspect, the directional system is adapted to detect (such as adaptively detect) from which direction a particular part of the microphone signal originates. This may be achieved by using conventionally known methods. The signal processing unit may include amplifier that is adapted to apply a frequency dependent gain to the input audio signal. The signal processing unit may further be adapted to provide other relevant functionality such as compression, noise reduction, etc. The output unit may include an output transducer such as a loudspeaker/receiver for providing an air-borne acoustic signal transcutaneously or percutaneously to the skull bone or a vibrator for providing a structure-borne or liquid-borne acoustic signal. In some hearing devices, the output unit may include one or more output electrodes for providing the electric signals such as in a Cochlear Implant.

A "cochlear implant hearing aid system" represents a particular type of "hearing system" comprising an external unit, which receives acoustic sound and processes the acoustic sound into a coded audio signal, and an implantable unit, receives the coded audio signal.

Now referring to FIG. 1, which illustrates a schematic diagram of a cochlear implant hearing aid system according to a first embodiment of the disclosure, i.e. a cochlear implant hearing aid system with a measuring unit configured to measure a dissipative current.

Particularly, according to FIG. 1, a cochlear implant hearing aid system 100 is disclosed. The system 100 comprises an external unit 110 (diagram according to FIG. 1 exclusive implantable unit 120) configured to receive acoustic sound and process the acoustic sound into a coded audio signal, and an implantable unit 120 configured to receive the coded audio signal. Further, the external unit 110 comprises a power supply unit 111 connected via a first path to a switching unit 112, wherein the switching unit 112 is connected via a second path to ground and is connected at an output thereof to a first coil 113. Furthermore, the switching unit 112 is configured to operate as a switching element configured to switch between switching states, wherein the switching states include a first state for applying and a second state for not applying a current to the first coil 113. The coded audio signal is supplied to the switching unit 112 as a control signal, and the first coil 113 is inductively linked to a second coil 121 arranged in the implantable unit 120. The system 100 further comprises a measuring unit 130 connected to the first path and configured to measure a dissipative current occurring in relation to the switching states of the switching unit 112, wherein the first path further comprises a shunt resistor 114, and the measuring unit 130 is configured to measure the dissipative current across the shunt resistor 114. Based on the measured dissipative current, a resonance frequency of the inductive link between the first and second coils 113, 121 is adapted.

A measuring element 135 is arranged in the measuring unit 130 for schematically illustrating a measurement performed by the measuring unit 130. In addition, a feedback control mechanism (dashed arrow according to FIG. 1) is indicated, running from the measuring unit 135 to the switching unit 112, enabling to continuously monitor the resonance frequency adaptation. Further, the second path comprises at least one of a coil and a resistor.

This allows for adapting the resonance frequency based on a measured dissipative current.

Particularly, such cochlear implant hearing aid system 100 further allows for measuring a tuning/mistuning of the switching unit 112. As a result thereof, by usage of one measurement, it is directly derivable which type of first and second coils 113, 121 to use for establishing the inductive link between the external unit 110 and the implantable unit 120, thereby for example addressing patients with different skin thicknesses by distinguishing e.g. between skin thickness ranges of 1 mm to 6 mm and 4 mm to 11 mm.

Specifically, the cochlear implant hearing aid system 100 further allows for monitoring an adaptation of the resonance frequency, and even further allows for continuously monitoring the adaptation during use of the cochlear implant hearing aid system 100, which is unique for a cochlear implant hearing aid system. This leads to even further improve power efficiency of the system 100, since the inductive link becomes more efficient due to the ability of continuously adapting the resonance frequency (keeping the resonance frequency of the first coil 121 aligned or almost aligned to a target resonance frequency). In particular, the resonance frequency of the first coil 121 is adapted in order to minimize the measured dissipative current.

As result of continuously monitoring a resonance frequency adaptation, adaptation of the resonance frequency (tuning of the switching unit 112) may be performed in real time, allowing for reducing power losses even further.

The system 100 according to FIG. 1 further allows for simplicity of a design of the measuring unit 130, by exploiting existing components of the switching unit 112 and/or the cochlear implant hearing aid system 100. Particularly, by using the existing components, application of new components to the switching unit 112/cochlear implant hearing aid system 100 is therefore avoidable, which leads to a more complex design of the measuring unit 130.

Additionally, the system 100 according to FIG. 1 further allows for avoiding that measuring unit 130 has an impact on the switching unit 112 in adapting the resonance frequency (an impact on tuning of the switching unit). Moreover, such cochlear implant hearing aid system 100 allows for avoiding that measuring unit 130 creates a parasitic resistance to the circuitry constituting the switching unit 112/cochlear implant hearing aid system 100.

Figure 2:
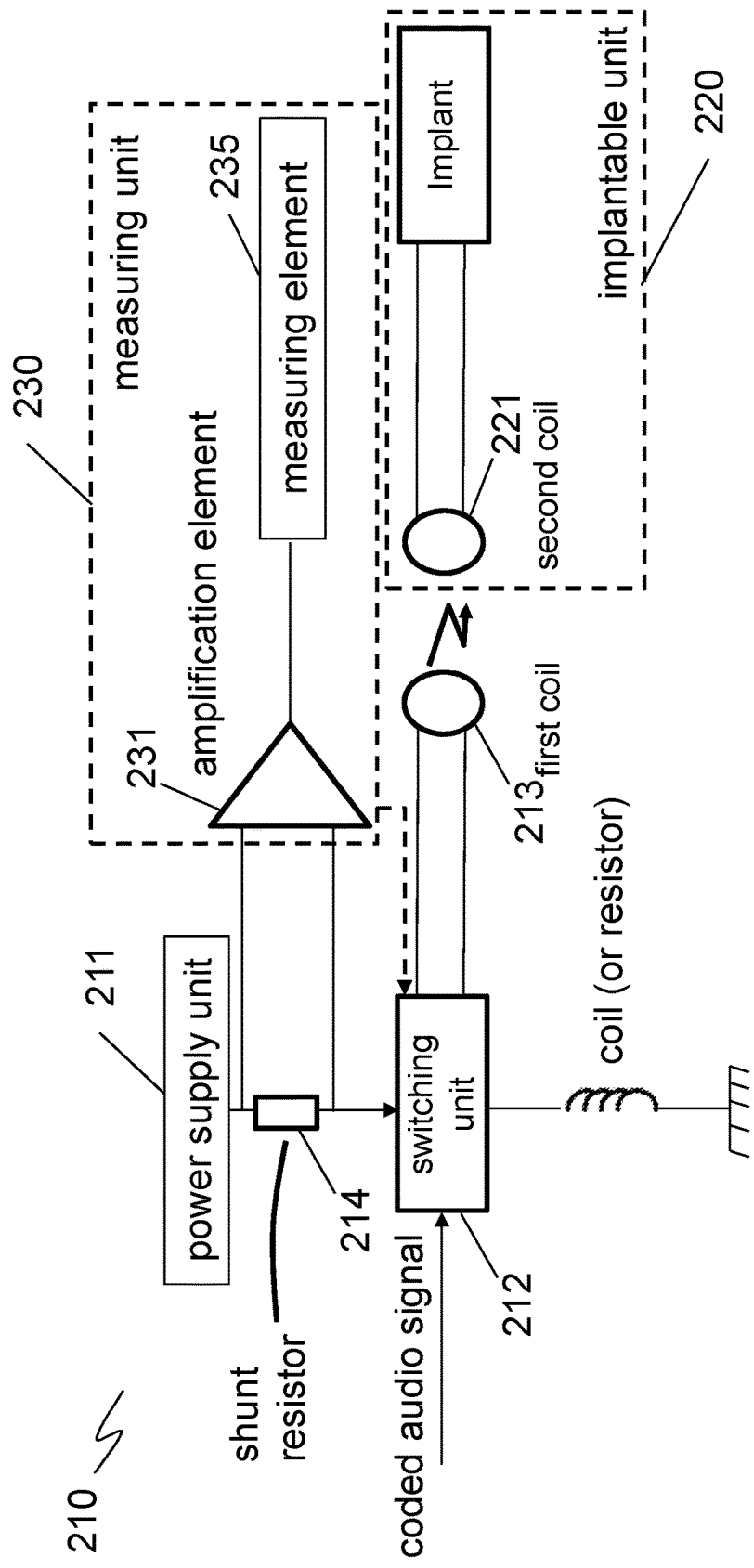
FIG. 2 illustrates a schematic diagram of a cochlear implant hearing aid system according to the first embodiment of the disclosure.

FIG. 2 illustrates a schematic diagram of a cochlear implant hearing aid system 200 according to the first embodiment of the disclosure. Particularly, FIG. 2 differs from FIG. 1 in that FIG. 2 illustrates a measuring unit 230 with an alternative structure in comparison to the measuring unit 130 according to FIG. 1. Specifically, the measuring unit 230 according to FIG. 2 may further comprise an amplification element 231 configured to amplify a current to be measured by the measuring unit 230.

Due to the amplification, this allows for easier measurement of the dissipative current, as well as for reducing measurement errors based on background noise. Regarding a quality of the inductive link between the first coil 113 and the second coil 121, the higher the measured current, the worse the inductive link, because more current is drawn from the power supply unit 111 for being able to transmit the coded audio signal.

Figure 3:
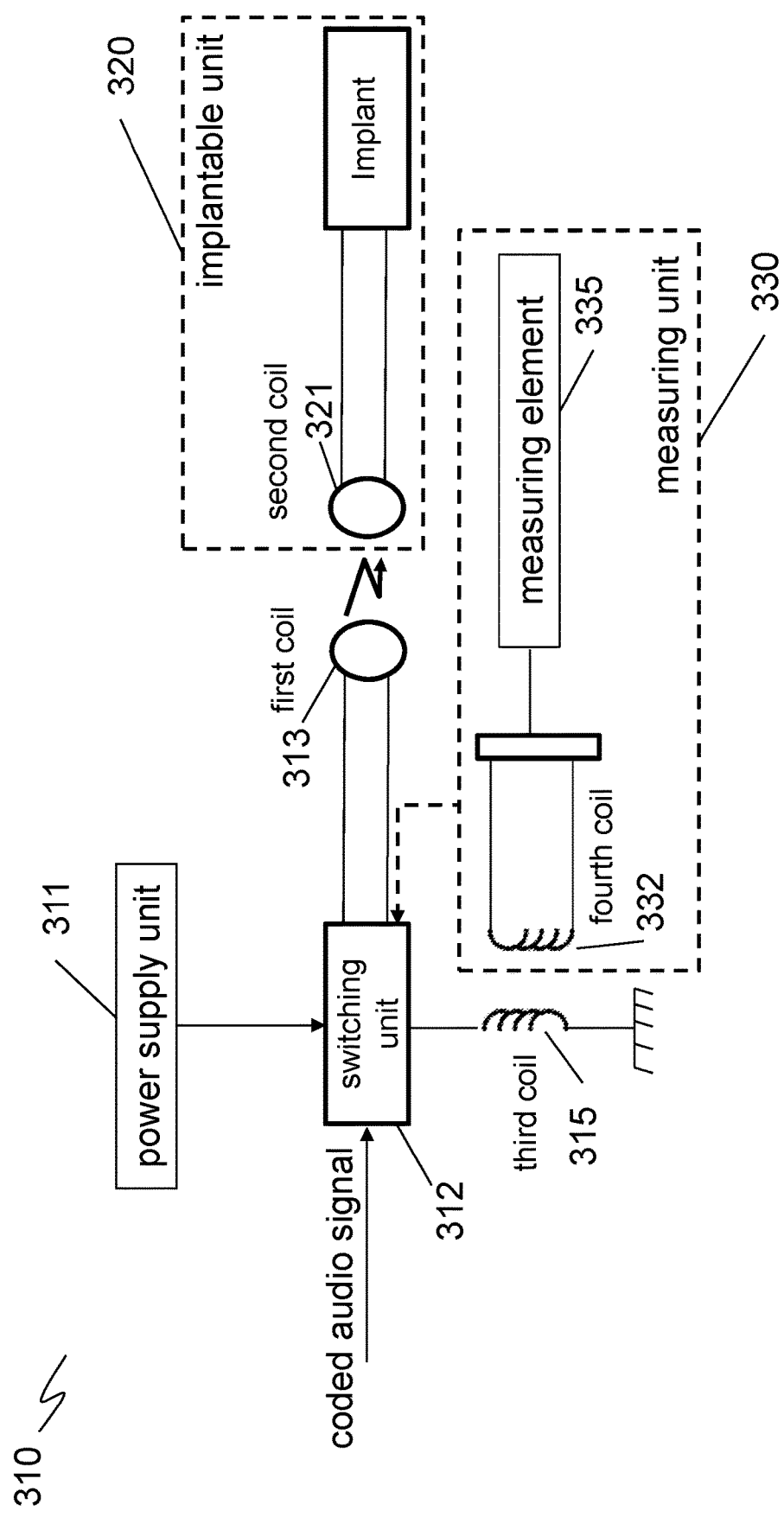
FIG. 3 illustrates a schematic diagram of a cochlear implant hearing aid system according to a second embodiment of the disclosure.

Referring to FIG. 3, FIG. 3 illustrates a schematic diagram of a cochlear implant hearing aid system according to a second embodiment of the disclosure, i.e. a cochlear implant hearing aid system with a measuring unit configured to measure a dissipative current.

Particularly, according to FIG. 3, a cochlear implant hearing aid system 300 is disclosed. The system 300 comprises an external unit 310 (diagram according to FIG. 3 exclusive implantable unit 320) configured to receive acoustic sound and process the acoustic sound into a coded audio signal, and an implantable unit 320 configured to receive the coded audio signal. Further, the external unit 310 comprises a power supply unit 311 connected via a first path to a switching unit 312, wherein the switching unit 312 is connected via a second path to ground and is connected at an output thereof to a first coil 313. Furthermore, the switching unit 312 is configured to operate as a switching element configured to switch between switching states, wherein the switching states include a first state for applying and a second state for not applying a current to the first coil 313. The coded audio signal is supplied to the switching unit 312 as a control signal, and the first coil 313 is inductively linked to a second coil 321 arranged in the implantable unit 320. The system 300 further comprises a measuring unit 330 connected to the second path and configured to measure a dissipative current occurring in relation to the switching states of the switching unit 312, wherein the second path comprises a third coil 315 inductively coupled to a fourth coil 332, and the measuring unit 330 comprises the fourth coil 332. The measuring unit 330 is further configured to measure a current induced in the fourth coil 332 and to derive the dissipative current therefrom. Based on the measured dissipative current, a resonance frequency of the inductive link between the first and second coils 313, 321 is adapted.

A measuring element 335 is arranged in the measuring unit 330 for schematically illustrating a measurement performed by the measuring unit 330. In addition, a feedback control mechanism (dashed arrow according to FIG. 3) is indicated, running from the measuring unit 335 to the switching unit 312, enabling to continuously monitor the resonance frequency adaptation.

Similar to the first embodiment, the system 300 according to FIG. 3 allows for monitoring an adaptation of the resonance frequency in real time, therefore allowing to reduce power losses even further. Additionally, similar to the first embodiment, the system 300 according to FIG. 3 allows for simplicity of a design of the measuring unit 330, by exploiting existing components of the switching unit 312 and/or the cochlear implant hearing aid system 300.

Moreover, further similar to the first embodiment, this system 300 further allows for avoiding the measuring unit 330 to have an impact on the switching unit 312 adapting the resonance frequency (tuning of the switching unit), as well as for avoiding the measuring unit 330 to create a parasitic resistance to the circuitry constituting the switching unit 312/cochlear implant hearing aid system 300.

Figure 4:
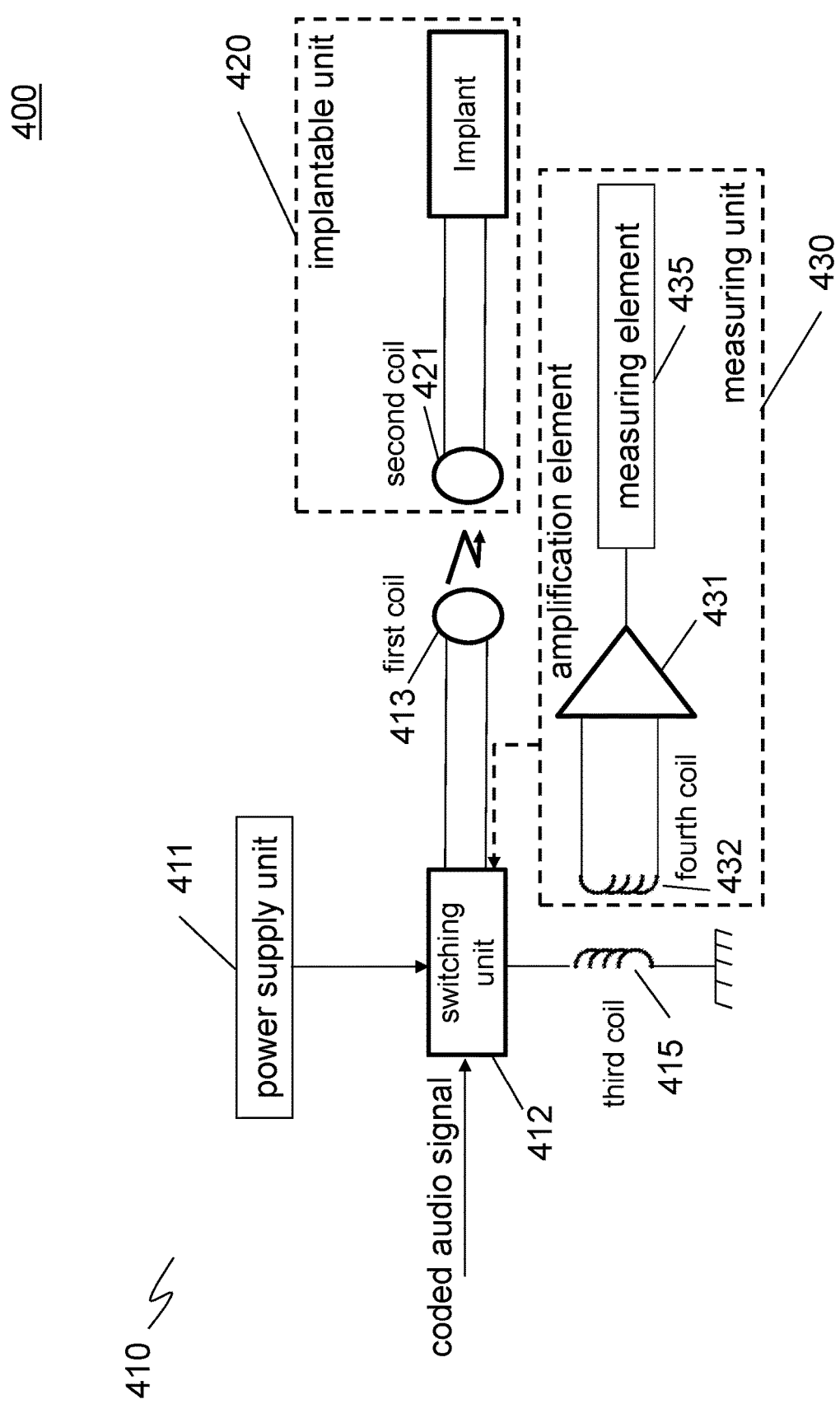
FIG. 4 illustrates a schematic diagram of a cochlear implant hearing aid system according to the second embodiment of the disclosure.

FIG. 4 illustrates a schematic diagram of a cochlear implant hearing aid system 400 according to the second embodiment of the disclosure. Particularly, FIG. 4 differs from FIG. 3 in that FIG. 4 illustrates a measuring unit 430 with an alternative structure in comparison to the measuring unit 330 according to FIG. 3. Specifically, the measuring unit 430 according to FIG. 4 may further comprise an amplification element 431 configured to amplify the current induced in the fourth coil 432.

Figure 5:
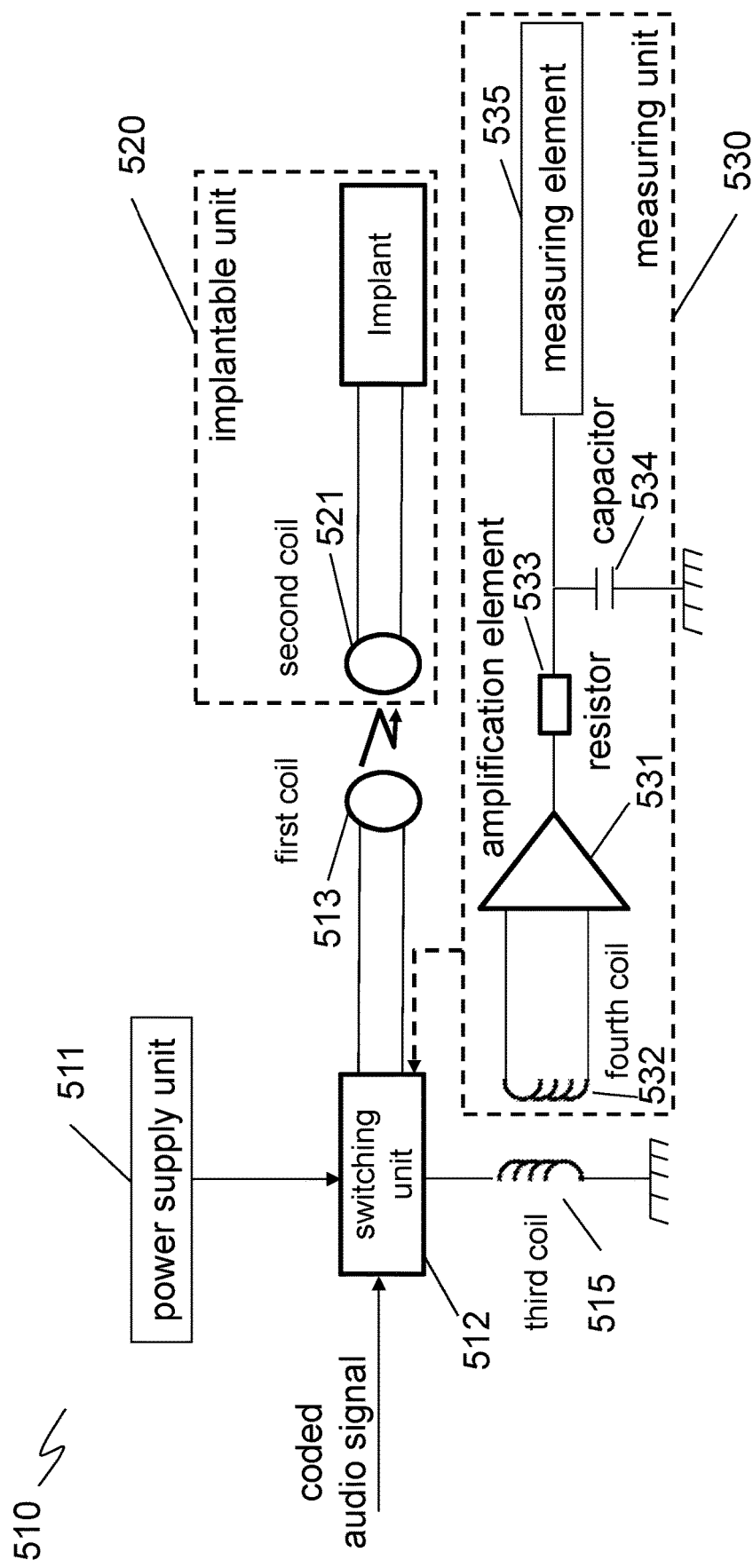
FIG. 5 illustrates a schematic diagram of a cochlear implant hearing aid system according to the second embodiment of the disclosure.

Furthermore, FIG. 5 illustrates a schematic diagram of a cochlear implant hearing aid system 500 according to the second embodiment of the disclosure. Particularly, FIG. 5 differs from FIGS. 3 and 4 in that FIG. 5 illustrates a measuring unit 530 with an alternative structure in comparison to the measuring units 330, 430 according to FIGS. 3 and 4. Specifically, in comparison to the measuring unit 430 according to FIG. 4, the measuring unit 530 according to FIG. 5 may further comprise a resistor 533 connected to an output of an amplification element 531 and a capacitor 534 connected at one out of its terminals to the connection between the output of the amplification element 531 and the resistor 533 and at the other one of its terminals to ground.

Similar to the first embodiment, due to the amplification, this allows for easier measurement of the dissipative current, as well as for reducing measurement errors based on background noise.

Specifically, regarding cochlear implant hearing aid system 500 according to FIG. 5, at maximum efficiency (perfect tuning), there is theoretically no current in a (not shown) drain of a transistor of the switching unit 512, thus there is no dissipative current. However, if the switching unit is mistuned, dissipative current occurs in the transistor, leading to power losses. The dissipative current will go through the third coil 515 and image of this dissipative current will be created in the fourth coil 523 because of the inductive coupling between the third and fourth coils 515, 523. The amplification element 531 provides an impedance adaptation between the very low impedance of the fourth coil 532 and the measurement circuit comprising the resistor 533 and the capacitor 534. The amplification element 531 amplifies the current (created image of the dissipative current) in the fourth coil 532. The current in the fourth coil 532 is an AC current with high frequency content. Thus, such current is complex to measure. Therefore, after the amplification by the amplification element 531, the resistor 533 and the capacitor 532 allow to create from this AC current a DC voltage (average value of the signal). As a result, a voltage used for determining the dissipative current may be effectively measured across the capacitor 534.

Figure 6:
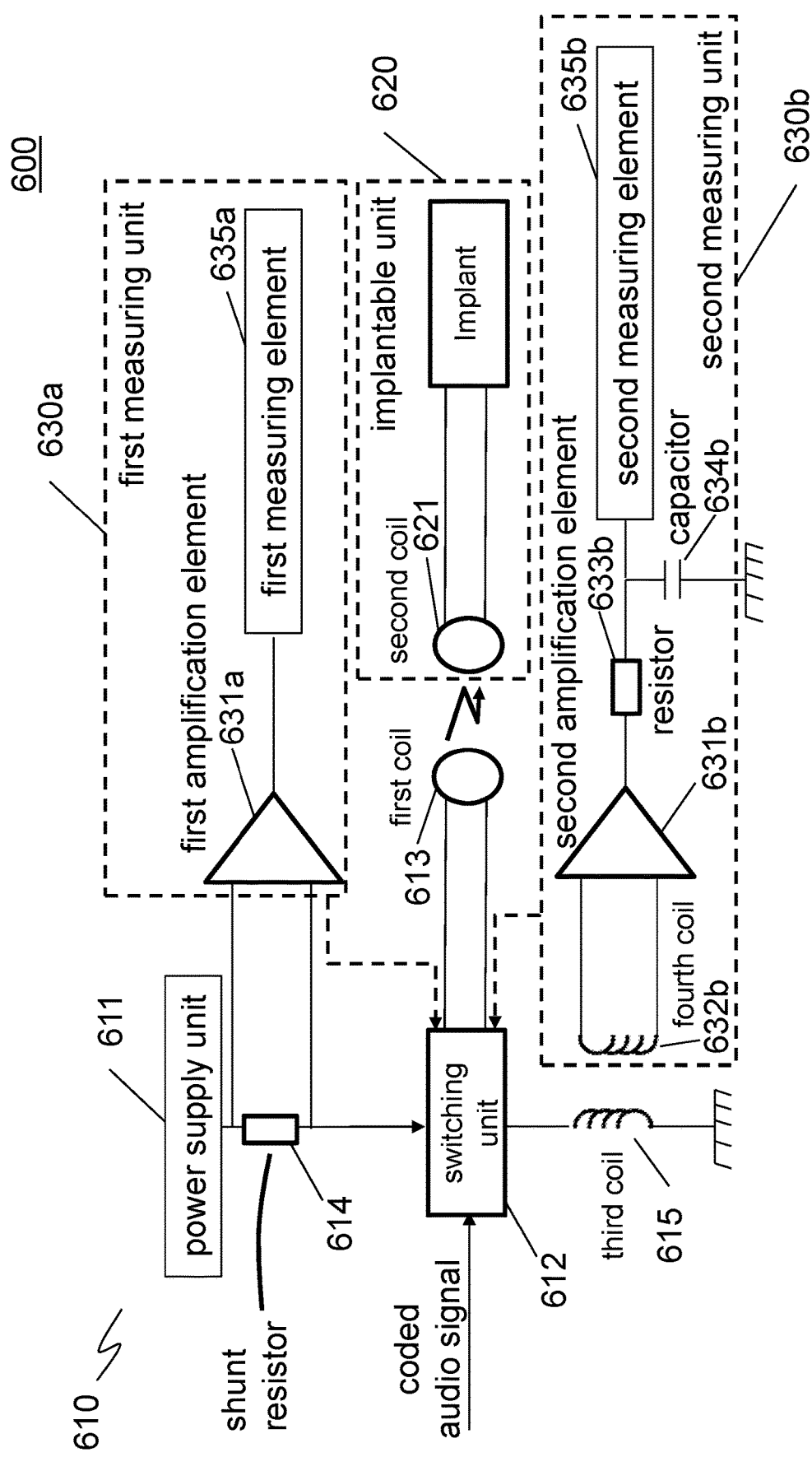
FIG. 6 illustrates a schematic diagram of a cochlear implant hearing aid system according to a third embodiment of the disclosure.

Referring to FIG. 6, FIG. 6 illustrates a schematic diagram of a cochlear implant hearing aid system 600 according to a third embodiment of the disclosure. In general, the third embodiment refers to combinations of the first and second embodiments. FIG. 6 illustrates a particular combination of the first and second embodiments.

Namely, according to FIG. 6, a cochlear implant hearing aid system 600 is disclosed. The system 600 comprises an external unit 610 (diagram according to FIG. 6 exclusive implantable unit 620) configured to receive acoustic sound and process the acoustic sound into a coded audio signal, and an implantable unit 620 configured to receive the coded audio signal. Further, the external unit 610 comprises a power supply unit 611 connected via a first path to a switching unit 612, wherein the switching unit 612 is connected via a second path to ground and is connected at an output thereof to a first coil 613. Furthermore, the switching unit 612 is configured to operate as a switching element configured to switch between switching states, wherein the switching states include a first state for applying and a second state for not applying a current to the first coil 613. The coded audio signal is supplied to the switching unit 612 as a control signal, and the first coil 613 is inductively linked to a second coil 621 arranged in the implantable unit 620.

The system 600 further comprises a first measuring unit 630*a* connected to the first path and configured to measure a first dissipative current occurring in relation to the switching states of the switching unit 612. The first measuring unit 630*a* further comprises a first amplification element 631*a* configured to amplify a current to be measured by the first measuring unit 630*a*. The first path further comprises a shunt resistor 614, and the first measuring unit 630*a* is configured to measure the first dissipative current across the shunt resistor 614.

In addition, the system 600 further comprises a second measuring unit 630*b* connected to the second path and configured to measure a second dissipative current occurring in relation to the switching states of the switching unit 612. The second path comprises a third coil 615 inductively coupled to a fourth coil 632*b*, and the second measuring unit 630*b* comprises the fourth coil 632*b*. In addition, the second measuring unit 630*b* further comprises a second amplification element 631*b* configured to amplify the current induced in the fourth coil 632*b*. Moreover, the second measuring unit 630*b* further comprises a resistor 633*b* connected to an output of a the second amplification element 631*b* and a capacitor 634*b* connected at one out of its terminals to the connection between the output of the second amplification element 631*b* and the resistor 633*b* and at the other one of its terminals to ground. Further, the second measuring unit 630b is configured to measure a current induced in the fourth coil 632b and to derive the second dissipative current therefrom.

A first measuring element 635a is arranged in the first measuring unit 630a for schematically illustrating a measurement performed by the first measuring unit 630a and a second measuring element 635b is arranged in the second measuring unit 630b for schematically illustrating a measurement performed by the second measuring unit 630b. In addition, a feedback control mechanisms (dashed arrows according to FIG. 6) are indicated, running from the measuring units 635a, 635b to the switching unit 612, enabling to continuously monitor the resonance frequency adaptation and/or allowing further assessing/evaluation of the measured dissipative currents.

According to the cochlear implant hearing aid system 600 as illustrated in FIG. 6, based on at least one of the first and second measured dissipative current, a resonance frequency of the inductive link between the first and second coils 613, 621 is adapted.

In addition to the first and second embodiments, the cochlear implant hearing aid system 600 according to FIG. 6 further allows for, basically, comparing the first and second measured dissipative currents in order to even further improve a tuning of the switching unit 612 based on a result of the comparison. For example, the system 600 according to FIG. 6 allows for deriving a weighted dissipative current from the measured first and second dissipative currents based on applying a predetermined weighting algorithm. As a result for example, an effect of background noise may be reduced. Therefore, the resonance frequency of the inductive link may be adapted based on the derived weighted dissipative current.

Such predetermined weighting algorithms are for example the following, but not limited thereto, averaging the first and second measured dissipative currents (weighting of 50% per measured current), selecting only the measured dissipative current of highest/lowest intensity (weighting of 100% for one measured current), or weighting the first and second measured dissipative currents relative to respective measured intensities.

Moreover, according to various exemplary embodiments, the switching unit 112, 212, 312, 412, 512, 612 may be for example an E-Class amplifier.

An E-Class amplifier is an amplifier that uses resonating load in order to minimize loss and allows for a theoretical maximum efficiency of 100%. This is achieved by having no losses during transistor switches performed by a transistor contained by the E-Class amplifier. Thus, if a current dissipated by the transistor is relatively small, the E-Class amplifier is well-tuned (the resonance frequency is well-adapted). However, if the current dissipated by the transistor comprises for example larger spike currents than in the well-tuned case, the E-Class amplifier is mistuned (the resonance frequency adapted incorrectly).

Therefore, such E-Class amplifier allows for theoretically 100% efficiency of the switching unit 112, 212, 312, 412, 512, 612, which means no power losses and, therefore, no dissipative current.

Figure 7:
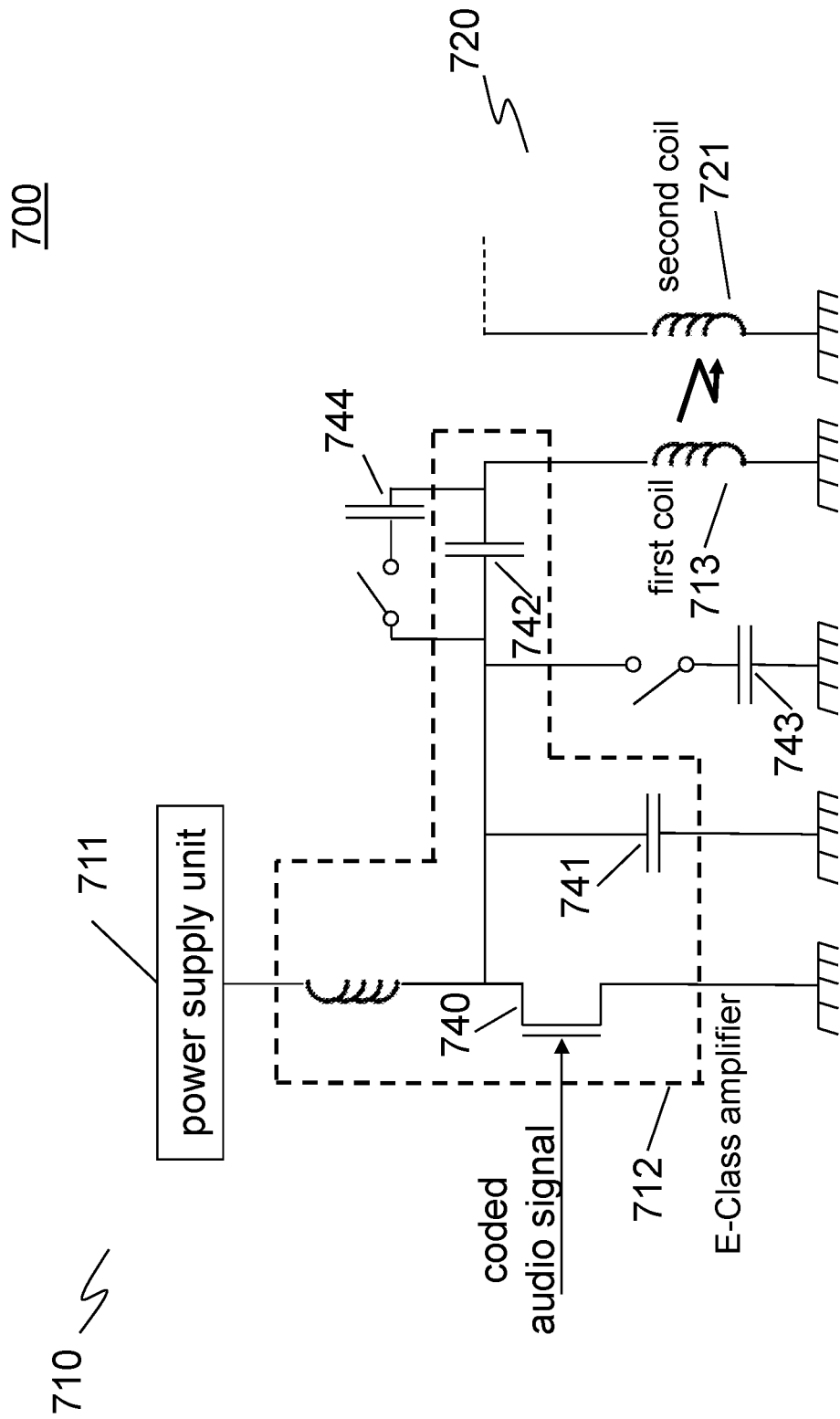
FIG. 7 illustrates a method for a cochlear implant hearing aid system according to embodiments of the disclosure.

Referring to FIG. 7, FIG. 7 illustrates a cochlear implant hearing aid system 700 where the switching unit 712 is an E-Class amplifier, and tuning of the E-Class amplifier 712 is performed via switched capacitors 743, 744.

In addition, as an example with reference to FIG. 7, according to various exemplary embodiments, the resonance frequency of the inductive link may be adapted based on the at least one measured dissipative current by selectively connecting at least one further switched capacitor 743, 744 to a circuitry constituting the switching unit 112, 212, 312, 412, 512, 612, 712.

Additionally, according to various exemplary embodiments, the switching unit 112, 212, 312, 412, 512, 612, 712 may further comprise at least one of a first switched capacitor 743 and a second switched capacitor 744, wherein the first switched capacitor 743 may be connected in parallel to a first circuitry element 741, and the second switched capacitor 744 may be connected in serial to a second circuitry element 742. Further, the resonance frequency may be adapted based on the at least one measured dissipative current by selectively connecting at least one of the first and second switched capacitors 743, 744 to the circuitry constituting the switching unit 112, 212, 312, 412, 512, 612, 712.

Furthermore, according to various exemplary embodiments, the switching unit 112, 212, 312, 412, 512, 612, 712 may further comprise a transistor element 740, wherein the transistor element 740 may be connected at an output thereof via the first circuitry element 741 to ground, and via the second circuitry element 742 to the first coil 713. Further, the first circuitry element 741 may be a third capacitor, and the second circuitry element 742 may be a fourth capacitor.

Based on the continuous monitoring process as outlined above, this allows for adjusting a tuning of the switching unit 112, 212, 312, 412, 512, 612, 712 in real time.

Regarding the switched capacitors 743, 744 is it to be understood that these two switched capacitors serve as an example, and that the switching unit 112, 212, 312, 412, 512, 612, 712 may comprise more than two such switched capacitors 743, 744 at different positions in the circuitry constituting the switching unit 112, 212, 312, 412, 512, 612, 712. Further, a switched capacitor, such as any of the first and second switched capacitor 743, 744 according to FIG. 7, may be an arrangement of a plurality of capacitors connected together in parallel or in serial or in any combination thereof. Therefore, allowing for fine-tuning of the switching unit 112, 212, 312, 412, 512, 612, 712.

Furthermore, multiple switch-capacitor pairs may be connected in parallel and in parallel to capacitor C2, e.g. a single switch-capacitor pair includes a switch and a capacitor. If a first switch-capacitor pair is turned on the remaining are turned off, the resonant frequency increases, and when turning a second switch-capacitor pair on and the remaining off, the resonant frequency increases even more. For example, when turning the first switch-capacitor pair on is ideal for a first skin thickness, and when turning the second switch capacitor pair on is ideal for a second skin thickness, wherein the second skin thickness is thicker than the first skin thickness.

Figure 8:
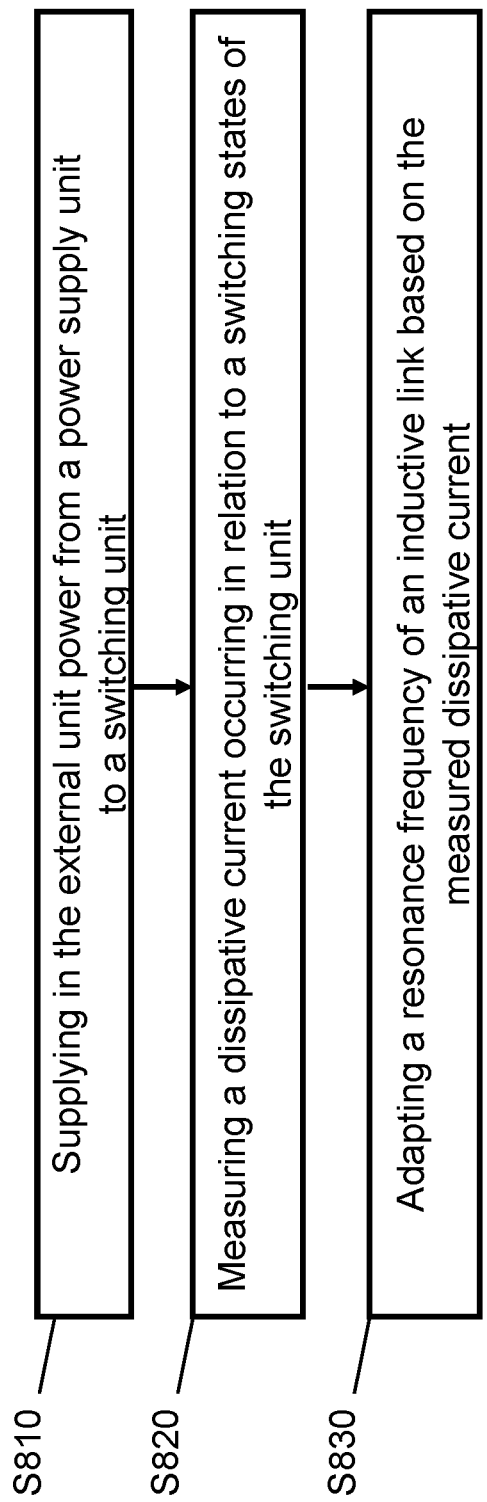
FIG. 8 illustrates tuning of an E-Class amplifier via switched capacitors.

Referring to FIG. 8, FIG. 8 illustrates a method for a cochlear implant hearing aid system according to embodiments of the disclosure. The method according to FIG. 8 may be executed by the cochlear implant hearing aid systems 100, 200, 300, 400, 500, 600, and 700 according to FIGS. 1, 2, 3, 4, 5, 6, and 7 respectively. However, the method is not limited thereto. Further, the cochlear implant hearing aid systems 100, 200, 300, 400, 500, 600 and 700 according to FIGS. 1, 2, 3, 4, 5, 6, and 7, respectively, may execute the method according to FIG. 8. However, the cochlear implant hearing aid systems 100, 200, 300, 400, 500, 600, and 700 are not limited thereto.

Particularly, according to FIG. 8, a method for a cochlear implant hearing aid system 100, 200, 300, 400, 500, 600, 700 comprising an external unit 110, 210, 310, 410, 510, 610, 710 receiving acoustic sound and processing the acoustic sound into a coded audio signal and an implantable unit 120, 220, 320, 420, 520, 620, 720 receiving the coded audio signal is disclosed. The method comprises the steps of supplying (Step S810) in the external unit 110, 210, 310, 410, 510, 610, 710 power from a power supply unit 111, 211, 311, 411, 511, 611, 711 via a first path to a switching unit 112, 212, 312, 412, 512, 612, 712 wherein the switching unit 112, 212, 312, 412, 512, 612, 712 is connected via a second path to ground and is connected at an output thereof to a first coil 113, 213, 313, 413, 513, 613, 713. Further, the switching unit 112, 212, 312, 412, 512, 612, 713 operates as a switching element to switch between switching states, wherein the switching states include a first state for applying and a second state for not applying a current to the first coil 113, 213, 313, 413, 513, 613, 713. The coded audio signal is supplied to the switching unit 112, 212, 312, 412, 512, 612, 712 as a control signal, and the first coil 113, 213, 313, 413, 513, 613, 713 is inductively linked to a second coil 121, 221, 321, 421, 521, 621, 721 arranged in the implantable unit 120, 220, 320, 420, 520, 620, 720. The method further comprises the steps of measuring (Step S820) across at least one of the first and second paths a dissipative current occurring in relation to the switching states of the switching unit 112, 212, 312, 412, 512, 612, 712. The method further comprises adapting (Step S830) a resonance frequency of the inductive link between the first and second coils 113, 213, 313, 413, 513, 613; 121, 221, 321, 421, 521, 621, 721 based on the at least one measured dissipative current.

This allows for a method for measuring a dissipative current, by exploiting existing components of the switching unit 112, 212, 312, 412, 512, 612, 712 and/or the cochlear implant hearing aid system 100, 200, 300, 400, 500, 600, 700. Particularly, by applying the method on the existing components, application of new components to the switching unit 112, 212, 312, 412, 512, 612, 712/cochlear implant hearing aid system 100, 200, 300, 400, 500, 600, 700 is therefore avoided, which leads to a more simplified measurement.

In addition, according to various exemplary embodiments, the method may further comprise the steps of measuring a first dissipative current across a shunt resistor 114, 214, 614 contained in the first path, and/or measuring a second dissipative current based on a current induced in a fourth coil 332, 432, 532, 632b inductively coupled to a third coil 315, 415, 515, 615, wherein the third coil 315, 415, 515, 615 is comprised in the second path.

This further allows for a method for avoiding the measurement to have an impact on a tuning of the switching unit 112, 212, 312, 412, 512, 612, as well as for avoiding the measurement to create a parasitic resistance to the circuitry constituting the switching unit 112, 212, 312, 412, 512, 612, 712/cochlear implant hearing aid system 100, 200, 300, 400, 500, 600, 700.

Furthermore, according to various exemplary embodiments, the method may further comprise the steps of deriving a weighted dissipative current from the measured first and second dissipative currents based on applying a predetermined weighting algorithm. Further, the method may comprise adapting the resonance frequency of the inductive link based on the derived weighted dissipative current.

Since for example an effect of background noise occurring in the measurements may be reduced, evaluating the first and second measured dissipative currents in combination allows for increasing accuracy in tuning of the switching unit 112, 212, 312, 412, 512, 612, 712.

Moreover, according to various exemplary embodiments, the method may further comprise the steps of adapting the resonance frequency of the inductive link based on the at least one measured dissipative current by selectively connecting at least one further switched capacitor to a circuitry constituting the switching unit 112, 212, 312, 412, 512, 612, 712.

Additionally, according to various exemplary embodiments, the switching unit 112, 212, 312, 412, 512, 612, 712 may further comprise at least one of a first switched capacitor and a second switched capacitor. The first switched capacitor is connected in parallel to a first circuitry element, and the second switched capacitor is connected in serial to a second circuitry element. The method may further comprises the steps of adapting the resonance frequency of the inductive link based on the at least one measured dissipative current by selectively connecting at least one of the first and second switched capacitors to the circuitry constituting the switching unit 112, 212, 312, 412, 512, 612, 712. The switching unit 112, 212, 312, 412, 512, 612, 712 may be an E-Class amplifier and may further comprise a transistor element, wherein the transistor element is connected at an output thereof via the first circuitry element to ground, and at an output thereof via the second circuitry element to the first coil. The first circuitry element may be a third capacitor and the second circuitry element may be a fourth capacitor.

This allows for a method for adjusting a tuning of the switching unit 112, 212, 312, 412, 512, 612, 712 in real time.

A Cochlear Implant typically includes i) an external part for picking up and processing sound from the environment, and for determining sequences of pulses for stimulation of the electrodes in dependence on the current input sound, ii) a (typically wireless, e.g. inductive) communication link for simultaneously transmitting information about the stimulation sequences and for transferring energy to iii) an implanted part allowing the stimulation to be generated and applied to a number of electrodes, which are implantable in different locations of the cochlea allowing a stimulation of different frequencies of the audible range. Such systems are e.g. described in U.S. Pat. Nos. 4,207,441 and in 4,532,930.

In an aspect, the hearing device comprises multi-electrode array e.g. in the form of a carrier comprising a multitude of electrodes adapted for being located in the cochlea in proximity of an auditory nerve of the user. The carrier is preferably made of a flexible material to allow proper positioning of the electrodes in the cochlea such that the electrodes may be inserted in cochlea of a recipient. Preferably, the individual electrodes are spatially distributed along the length of the carrier to provide a corresponding spatial distribution along the cochlear nerve in cochlea when the carrier is inserted in cochlea.

In an aspect, the functions may be stored on or encoded as one or more instructions or code on a tangible computer-readable medium. The computer readable medium includes computer storage media adapted to store a computer program comprising program codes, which when run on a processing system causes the data processing system to perform at least some (such as a majority or all) of the steps of the method described above, in the and in the claims.

By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, includes compact disc (CD), laser disc, optical disc, digital versatile disc (DVD), floppy disk and Blu-ray disc where disks usually reproduce data magnetically, while discs reproduce data optically with lasers. Combinations of the above should also be included within the scope of computer-readable media. In addition to being stored on a tangible medium, the computer program can also be transmitted via a transmission medium such as a wired or wireless link or a network, e.g. the Internet, and loaded into a data processing system for being executed at a location different from that of the tangible medium.

Regarding the above described method, adjustment of the resonance frequency may be implemented in software.

In an aspect, a data processing system comprising a processor adapted to execute the computer program for causing the processor to perform at least some (such as a majority or all) of the steps of the method described above and in the claims.

Regarding the above described method, adjustment of the resonance frequency may be implemented in software.

It is intended that the structural features of the devices described above, either in the detailed description and/or in the claims, may be combined with steps of the method, when appropriately substituted by a corresponding process.

As used, the singular forms "a," "an," and "the" are intended to include the plural forms as well (i.e. to have the meaning "at least one"), unless expressly stated otherwise. It will be further understood that the terms "includes," "comprises," "including," and/or "comprising," when used in this specification, specify the presence of stated features, integers, steps, operations, elements, and/or components, but do not preclude the presence or addition of one or more other features, integers, steps, operations, elements, components, and/or groups thereof. It will also be understood that when an element is referred to as being "connected" or "coupled" to another element, it can be directly connected or coupled to the other element but an intervening elements may also be present, unless expressly stated otherwise. Furthermore, "connected" or "coupled" as used herein may include wirelessly connected or coupled. As used herein, the term "and/or" includes any and all combinations of one or more of the associated listed items. The steps of any disclosed method is not limited to the exact order stated herein, unless expressly stated otherwise.

It should be appreciated that reference throughout this specification to "one embodiment" or "an embodiment" or "an aspect" or features included as "may" means that a particular feature, structure or characteristic described in connection with the embodiment is included in at least one embodiment of the disclosure. Furthermore, the particular features, structures or characteristics may be combined as suitable in one or more embodiments of the disclosure. The previous description is provided to enable any person skilled in the art to practice the various aspects described herein. Various modifications to these aspects will be readily apparent to those skilled in the art, and the generic principles defined herein may be applied to other aspects.

The claims are not intended to be limited to the aspects shown herein, but is to be accorded the full scope consistent with the language of the claims, wherein reference to an element in the singular is not intended to mean "one and only one" unless specifically so stated, but rather "one or more." Unless specifically stated otherwise, the term "some" refers to one or more.

Accordingly, the scope should be judged in terms of the claims that follow.

The invention claimed is:

1. A cochlear implant hearing aid system, comprising:
an external unit configured to receive acoustic sound and process the acoustic sound into a coded audio signal,
an implantable unit configured to receive the coded audio signal,
wherein the external unit comprises:
a power supply unit connected via a first path to a switching unit, wherein:
the switching unit is connected via a second path to ground, is connected at an output thereof to a first coil, and the switching unit is configured to operate as a switching element configured to switch between switching states, wherein the switching states include a first state for applying and a second state for not applying a current to the first coil, wherein the coded audio signal is supplied to the switching unit as a control signal, wherein
the first coil is inductively linked to a second coil arranged in the implantable unit,
a measuring unit connected to at least one of the first and second paths and configured to measure a dissipative current occurring in relation to the switching states of the switching unit, wherein
based on the at least one measured dissipative current, a resonance frequency of the inductive link between the first and second coils is adapted;
wherein the second path further comprises a third coil inductively coupled to a fourth coil, and the measuring unit comprises the fourth coil and is further configured to measure the current induced in the fourth coil and to derive the dissipative current therefrom, and
wherein the measuring unit is further configured to comprise an amplification element configured to amplify the current induced in the fourth coil.

2. The cochlear implant hearing aid system according to claim 1,
wherein the first path further comprises a shunt resistor, and the measuring unit is further configured to measure the dissipative current across the shunt resistor.

3. The cochlear implant hearing aid system according to claim 2,
wherein the measuring unit further comprises an amplification element configured to amplify the dissipative current to be measured by the measuring unit.

4. The cochlear implant hearing aid system according to claim 1,
wherein the measuring unit is further configured to comprise a resistor connected to an output of the amplification element and a capacitor connected at one out of its terminals to the connection between the output of the amplification element and the resistor and at the other one of its terminals to ground.

5. The cochlear implant hearing aid system according to claim 1,
wherein the switching unit is an E-Class amplifier.

6. The cochlear implant hearing aid system according to claim 5, wherein
the resonance frequency of the inductive link is adapted based on the at least one measured dissipative current by selectively connecting at least one further switched capacitor to a circuitry constituting the switching unit.

7. The cochlear implant hearing aid system according to claim 1, wherein
the resonance frequency of the inductive link is adapted based on the at least one measured dissipative current by selectively connecting at least one further switched capacitor to a circuitry constituting the switching unit.

8. The cochlear implant hearing aid system according to claim 7, wherein the switching unit further comprises at least one of a first switched capacitor and a second switched capacitor, wherein
the first switched capacitor is connected in parallel to a first circuitry element, and
the second switched capacitor is connected in serial to a second circuitry element, and
the resonance frequency is adapted based on the at least one measured dissipative current by selectively connecting at least one of the first and second switched capacitors to the circuitry constituting the switching unit.

9. The cochlear implant hearing aid system according to claim 8, wherein
the switching unit further comprises a transistor element, wherein the transistor element is connected at an output thereof via the first circuitry element to ground, and via the second circuitry element to the first coil,
wherein the first circuitry element is a third capacitor, and the second circuitry element is a fourth capacitor.

10. A method for a cochlear implant hearing aid system comprising an external unit receiving acoustic sound and processing the acoustic sound into a coded audio signal and an implantable unit receiving the coded audio signal, wherein the method comprises the steps of:
supplying in the external unit power from a power supply unit via a first path to a switching unit, wherein:
the switching unit is connected via a second path to ground, is connected at an output thereof to a first coil, and the switching unit operates as a switching element to switch between switching states, wherein the switching states include a first state for applying and a second state for not applying a current to the first coil, wherein the coded audio signal being supplied to the switching unit as a control signal, and wherein the first coil being inductively linked to a second coil arranged in the implantable unit,
measuring across at least one of the first and second paths a dissipative current occurring in relation to the switching states of the switching unit,
adapting a resonance frequency of the inductive link between the first and second coils based on the at least one measured dissipative current;
measuring a first dissipative current across a shunt resistor contained in the first path and measuring a second dissipative current based on a current induced in a fourth coil inductively coupled to a third coil, wherein the third coil is comprised in the second path,
deriving a weighted dissipative current from the measured first and second dissipative currents based on applying a predetermined weighting algorithm, and
adapting the resonance frequency of the inductive link based on the derived weighted dissipative current.

11. The method for a cochlear implant hearing aid system according to claim 10, further comprising the steps of
adapting the resonance frequency of the inductive link based on the at least one measured dissipative current by selectively connecting at least one further switched capacitor to a circuitry constituting the switching unit.

12. The method for a cochlear implant hearing aid system according to claim 11, wherein the switching unit further comprises at least one of a first switched capacitor and a second switched capacitor, wherein the first switched capacitor is connected in parallel to a first circuitry element, and the second switched capacitor is connected in serial to a second circuitry element, the method further comprises the steps of
adapting the resonance frequency of the inductive link based on the at least one measured dissipative current by selectively connecting at least one of the first and second switched capacitors to the circuitry constituting the switching unit,
wherein the switching unit is an E-Class Amplifier and further comprises a transistor element, wherein the transistor element is connected at an output thereof via the first circuitry element to ground, and at an output thereof via the second circuitry element to the first coil, and/or
wherein the first circuitry element is a third capacitor and the second circuitry element is a fourth capacitor.

\* \* \* \* \*